United States Patent [19]
Friedman et al.

[11] Patent Number: 5,897,879
[45] Date of Patent: Apr. 27, 1999

[54] SUSTAINED-RELEASE PHARMACEUTICAL SYSTEM FOR THE DELIVERY OF ANTIOXIDANTS

[75] Inventors: Michael Friedman; Ron Kohen, both of Jerusalem, Israel

[73] Assignee: Yissum Research Development Co. of the Hebrew University of Jerusalem, Jerusalem, Israel

[21] Appl. No.: 08/732,489

[22] PCT Filed: May 3, 1995

[86] PCT No.: PCT/US95/05504

§ 371 Date: Jan. 7, 1997

§ 102(e) Date: Jan. 7, 1997

[87] PCT Pub. No.: WO95/29666

PCT Pub. Date: Nov. 9, 1995

[30] Foreign Application Priority Data

May 3, 1994 [IL] Israel ........................................ 109539

[51] Int. Cl.⁶ ..................................................... A61K 9/64
[52] U.S. Cl. ........................... 424/486; 424/472; 424/491
[58] Field of Search ................................... 424/486, 460, 424/469, 472, 491

[56] References Cited

U.S. PATENT DOCUMENTS

| | | | |
|---|---|---|---|
| 4,876,094 | 10/1989 | Benton et al. | 424/491 |
| 5,283,065 | 2/1994 | Doyon et al. | 424/467 |
| 5,300,304 | 4/1994 | Sheth et al. | 424/490 |

OTHER PUBLICATIONS

Joseph A. Bakan: Microencapsulation using coacervation/phase separation technique, pp. 83–105 in vol. II of Controlled Release Technologies: Methods, Theory, and Applications, Agis F. Kydonieus, Ed., CRC Press Inc. Boca Raton, Florida, (1985).

Leszek Krowczynski: Dosage forms with chemical or physical–chemical bounded drug, pp. 104–108 in Extended Release Dosage Forms, L. Krowczynski, Author, CRC Press, Inc. Boca Raton, Florida, (1983).

Ames, "Dietary Carcinogens–Oxygen Radicals and Degenerative Diseases", *Science*, 221:1256–1264 (1983).

Friedman, in *Sustained Release Granules*, Thesis, The Hebrew University of Jerusalem (1973).

Gutteridge, "Free Radicals in Disease Processes: Compilation of Cause and Consequence", *Free Rad. Res. Comm.*, 19:141–158 (1993).

Halliwell, "Current Status Review: Free radicals, reactive oxygen species and human disease: critical eval. with special reference to atherosclerosis", *Br. J. Exp. Path.*, 70:737–752 (1989).

Halliwell and Gutteridge, "Free Radicals in Biology and Medicine", *Free Rad. Biol. Med.*, 2nd ed, Clarendon Press, Oxford (1989).

Halliwell and Gutteridge, "Oxygen toxicity, oxygen radicals, transition metals and disease", *Biochem. J.*, 219:1–14 (1984).

Halliwell et al., Free radicals, antioxidants, and human disease: Where are we now? *J. Lab. Clin. Med.*, 119:598–620 (1992).

Harman, "The Free–Radical Theory of Aging", *Gerontology*, 23:476 (1968).

Ihler, "Erythocyte Carriers", *Pharmac. Ther.*, 20:151–155 (1983).

Johnston et al., "The Role of Superoxide Anion Generation in Phagocytic Bactericidal Activity", *J. Clin. Invest.*, 55:1357 (1975).

Harman, "The Free Radical Theory of Aging", in *Free Radicals in Biology*, vol. 4 (ed. W.A. Pryor), p. 255, Academic Press, London, (1989).

Hsieh et al., "Magnetic modulation of release of macromolecules from polymers", *Proc. Nat'l. Acad. Sci. USA*, 78:91863–91868 (1981).

Kohen and Chevion, "Paraquat toxicity is enhanced by iron and reduced by desferrioxamine in laboratory mice", *Biochem. Pharmacol.*, 34:1841–1843 (1985).

Kohen et al., "Antioxidant activity of carnosine, homocarnosine, and anserine present in muscle and brain", *Proc. Natl. Acad. Sci. USA*, 85:3175–3179 (1988).

Robinson, in *Recent Advances in Topical Drug Delivery: Rate Control*, (ed. Nimmo, WS) Edinburg, Churchill Livingston, p. 71 (1985).

Rubinstein and Robinson, in *Progress in Clinical Biochemistry and Medicine*, Springer–Verlay (1986).

Schach, in *Controlled Drug Delivery*, vol. 1, (ed. Burck, S.D.) Florida CRC Press, pp. 149–161 (1983).

Taylor and Davies, "Protein Oxidation and Loss of Protease Activity may Lead to Cataract Formation in the Aged Lens", *Free Rad. Bio. Med.*, 3:371–377 (1987).

Theeuwes, "Elementary Osmotic Pump", *J. Pharm. Scie.*, 64:1987–1990 (1975).

Turrens et al., "Protection against Oxygen Toxicity by Intravenous Injection of Liposome–entrapped Catalase and Superoxide Dismutase", *J. Clin. Invest.*, 73:87–95 (1984).

Tyrrell et al., "New Aspects of Liposomes" *Biochem. Biophys. Acta*, 57:359–367 (1976).

Yelton and Schariff, "Monoclonal Antibodies" Powerful New Tool in Biology and Medicine, *Ann. Rev. Biochem*, 50:657–680 (1981).

*Primary Examiner*—Thurman K. Page
*Assistant Examiner*—Kathryne E. Shelborne
*Attorney, Agent, or Firm*—Kohn & Associates

[57] ABSTRACT

The invention relates to a sustained-release pharmaceutical delivery system for the administration of an antioxidant drug to a patient in need of such drug, wherein said delivery system comprises said drug in combination with a polymeric matrix, said matrix comprising a polymer which does not interact with said drug or a mixture of such polymers. The pharmaceutical delivery system of the invention is useful for the treatment of pathological conditions involving pathologically increased formation of active oxygen species.

13 Claims, No Drawings

SUSTAINED-RELEASE PHARMACEUTICAL SYSTEM FOR THE DELIVERY OF ANTIOXIDANTS

This application is a 371 of PCT/US95/05504 filed May 3, 1995.

FIELD OF THE INVENTION

The invention relates to sustained-release pharmaceutical delivery system comprising a low molecular weight antioxidant drug in combination with a polymeric matrix, in various dosage forms.

BACKGROUND OF THE INVENTION

In the last decade the role of oxygen free radicals as well as other oxygen reactive metabolites has been at least somewhat elucidated. These reactive metabolites are today considered to be responsible for oxidative toxicity in mammals and resulting the biological damage [Halliwell, B. and Gutteridge, J. M. C. (1989) Free Rad. Biol. Med. (2nd ed.) Clarendon Press, Oxford; Halliwell, B. (1989) Br. J. Exp. Path. 70: 737–752].

Free radicals are defined as an atom, group of atoms or molecule which contain at least one unpaired electron in their outer shell. The oxygen molecule itself, containing two unpaired electrons is, by definition, a free radical ($^3\Sigma_g O_2$—biradical), although it is not a reactive one due to the arrangement of its spins it its outer shell. Reduction of the oxygen molecule is a process which does not require changes in the spin direction of movement and therefore can be easily performed.

The complete reduction of the oxygen molecule results, at the first stage, in the production of the ion radical superoxide ($O_2^-$), followed by the production of hydrogen perxide ($H_2O_2$) which is not a free radical, although a reactive species. Addition of another electron to the hydrogen peroxide leads to the production of the hydroxyl radical (OH*), a highly reactive species [Halliwell and Gutteridge (1989) ibid.]. Such a process occurs in the mitochondria for energy generation [Halliwell (1989) ibid.]. In this system which contains cytochrome oxidase, the oxygen is reduced in stages. During the reduction of the oxygen molecule, active metabolites are produced. These active oxygen species can leak to the immediate surroundings and may cause biological damage.

The production of oxygen reactive metabolites is not unique to the mitochondria organ, but occurs also in many other systems. Phagocytes, for example, are known for their ability to produce the superoxide radical and other species which participate in the defence mechanism against invaders (phgocytosis) [Halliwell and Gutteridge (1989) ibid.]. This process, although necessary, can also lead to biological damage in the surrounding environment. Production of the superoxide radical has been identified in liver Kupffer cells, in monocytes, basophyls, eosinofils and mast cells. In some genetic disorders, such as chronic granulomatosus disease (CGD), the phagocytes are incapable of producing the oxygen radicals and consequently the patients suffer from recurring infections which can lead to death [Johnston, Jr., R. B. et al. (1975) J. Clin. Invest. 55: 1357]. Another source for free radicals are enzymes. During their catalytic activity many enzymes such as prolyl hydroxylase, lipoxygenase and cyclooxygenase, produce oxygen free radicals [Halliwell and Gutteridge (1989) ibid.].

Amongst the diseases in which free radicals have been shown to play an important role in the initiation and pathogenesis, one can find chronic inflammation, autoimmune diseases such as Hashimoto's thyroiditis, systemic lupus erythematosus, myasthenia gravis, chronic autoimmune gastritis, dermatomyositis, etc. [Gutteridge, J. M. C. (1993) Free Rad. Res. Comms. 19: 141–158]. Release of a free radicals efflux by the phagocytes can increase the severity of these diseases. This is the case, for example, in rheumatoid arthritis which is characterized by chronic inflammation of the joints. In this disease, the production of the inter-joint fluid is normal, but its viscosity is changed. The major constitutent of the inter-joint fluid, hyaluronic acid, is broken down into short fragments by the oxygen reactive species [Halliwell and Gutteridge (1989) ibid.].

It has been proposed that free radicals are involved in the damage caused to the brain in brain degenerative diseases such as epilepsy, Parkinson's disease, Wilson's disease (the excess of copper in this disorder causes the transformation of the superoxide radical into a more reactive species, the hydroxyl radical, in the metal-mediated Haber-Weiss reaction) [Halliwell, B. and Gutteridge J. M. C. (1984) Biochem. J. 219: 1–14]. It has also been suggest that free radicals are involved in eye diseases such as cataract and retinopathy [Taylor, A. and Davies, K. J. A. (1987) Free Rad. Biol. Med. 3: 371–377].

It has recently been demonstrated that oxygen driven free radicals play an important role in the post-ischemic damage to various biological tissues such as heart and brain. It has further been suggested that these metabolites take part in the aging process and age-related diseases such as amyloid generation, age pigmentation, neuron damage [Gutteridge (1993) ibid.]

Exposure of humans to free radicals is not limited to the endogenous oxygen free radical, but also to exogenous sources. Various agrochemicals can serve as free radical generation systems as in the case of the herbicide Paraquat [Kohen, R. and Chevion, M. (1985) Biochem. Pharmacol. 34: 1841–1843]. Other substances such as alloxan, isouramil, cigarette smoke, air pollutants, carcinogenic and mutagenic agents and many drugs can generate oxygen free metabolites and cause biological damage.

Exposure of living cells to continuous efflux of oxygen free radicals and reactive species led to their adaptation to living in an aerobic atmosphere. This adaptation process led to the development of several defence lines against the damage induced by these metabolites [Halliwell and Gutteridge (1989) ibid.; Ames, B. N. (1983) Science 221: 1256–1264]. The defence systems vary from one species to another and between different tissues of same species.

The broad definition of an antioxidant includes compounds which can cope with the oxidative stress by various mechanisms. Amongst the different kinds, one can find compounds which can protect fatty acids against oxidation and compounds which protect proteins, DNA and other important macromolecules. The different antioxidants can be classified as follows: compounds which donate hydrogen to the damaged target; compounds which scavenge free radicals; compounds which can bind the oxidants and remove them from the target; compounds which can convert reactive species to non-reactive metabolites; compounds which can protect through stabilization of biological membranes; reducing compounds which react with the oxidants; and compounds which are capable of binding mediators, such as transition metal ions, and prevent them from participating in the Haber-Weiss reaction [Kohen, R., et al. (1988) Proc. Natl. Acad. Sci. USA 85: 3175–3179].

In contrast to the antioxidant enzymes and some other antioxidants which are produced in humans, the antioxidant vitamins (E, C and A) are present only in the diet. New molecules which possess antioxidant activity were recently found in the muscle and brain [Kohen et al. (1988) ibid.]. Vitamins E and C, although not synthesized by humans, are essential for the functioning of many systems [Halliwell and Gutteridge (1989) ibid.]. Elimination of these antioxidants from the diet results in severe pathological symptoms. It has been shown in many pathological cases that administration of these antioxidants results in significant improvement [Halliwell and Gutteridge (1984) ibid.]. Patients undergoing irradiation therapy are given vitamin C in order to reduce some of the side effects involved with radiation. Administration of vitamin E and 2-mercaptoethylamine to rats resulted in a 30% increase of their life span [Herman, D. (1982) The Free Radical Theory of Aging. In: Free Radicals in Biology, Vol. V (ed. W. A. Pryor) p. 255, Academic Press, London; Herman, D. J. (1968) Gerontology 23: 476–450].

The enormous problems involved in using the se compounds, the difficulties in delivering them to their targets and the lack of knowledge in developing pharmaceutical dosage forms for these antioxidants, prevent their wide use in the treatment of diseases.

In order to prevent oxidative damage and due to the high reactivity of the oxygen reactive species, antioxidant molecules have to be present at the site of their biologocal targets in high concentrations and for long periods of time. To fulfill these requirements, sustained release dosage forms of antioxidant compounds are desirable.

Since the creation of the first pharmaceutical dosage forms in the early sixties, there has been a tremendous increase in the theoretical and practical development of such forms. The progress achieved in the treatment of many cancer forms over the last decade led to the urgent need for delivery and direction of drugs to their targets. There is considerable evidence that a constant level of the drug in its biological target results in decrease in the immediate and long term side effects and improves the therapeutical effects.

In contrast to conventional dosage forms, where the drug is released immediately after its administration, the advanced dosage forms allow the drug to be released in unique manners, as follows: (1) delayed-release dosage forms that significantly delay the release of the drug after its administration; (2) sustained-release dosage forms that prolong drug level in biological fluids and tissues; and (3) controlled-release dosage forms that release the drug at a constant rate.

Examples for release of the drug at a constant rate are the diffusion method [Rubinstein, A. and Robinson J. R. (1986) in: Progress in Clinical Biochemistry and Medicine, Springer-Verlay], the osmotic pressure method [Theeuwes, F. (1975) J. Pharm. Sci. 64: 1987–1990] and the ion-exchange method [Schach, E. H. (1983) in: Controlled Drug Delivery, Vol. 1 (ed. Burck, S. D.) Florida CRC Press, pp. 149–161].

Several approaches are sued in the design of sustained-release dosage forms, such as the mechanical approach and the prodrug approach. The mechanical approach is usually adopted when there is a demand for a large quantity of the drug over an extended period of time. Use of prodrug is most convenient when release of the drug at a specific target is desired. In this system, the drug in its active form is only obtained after chemical or enzymatic modification of the prodrug at the biological target site.

In order to deliver a drug to its target and to release it there at a constant rate, several methods have been developed, for example particulate methods such as microencapsulation, nanocapsules, drug embedded in matrix and microspheres [Robinson, T. R. (1985) in: Recent Advances in Topical Drug Delivery: Rate Control, (ed. Nimmo, W. S.) Edinburg, Churchill Livingstone, 71; Friedman, M. (1973) in: Sustained Release Granules, Thesis, The Hebrew University of Jerusalem]. Other methods involve the use of liposomes (such as for SOD and catalase [Tyrrell, D. A. et al. (1976) Biochim. Biophys. Acta 57: 359–367; Turrens, J. F. et al. (1984) J. Clin. Invest. 73: 87–95]) erythrocytes [Inhaler, G. M. (1983) Pharmac. Ther. 20: 151–155], monoclonal antibodies [Yelton, D. E. and Scharff, M. D. (1981) Ann. Rev. Biochem. 50: 657–680] and magnetic fields as a targeting tool [Hsieh, D. S. et al. (1981) Proc. Nat. Acad. Sci. USA 78: 91863–91868].

Many attempts to interfere with the oxidative reactions by using novel antioxidants and by removing the reactive species have been carried out and are reviewed in the literature [see, for example, Halliwell, B. et al. (1992) J. Lab. Clin. Med. 119: 598–620]. The limited success reported in many of these attempt resulted, in part, from the difficulties in introducing the antioxidants into cells and biological tissues and thus increases their level at the needed site. In order to prevent oxidative stress antioxidants have to be present in high concentrations and for long periods of time at their biological targets. The present invention is directed to such sustained release pharmaceutical dosage forms.

SUMMARY OF THE INVENTION

The invention relates to a sustained-release pharmaceutical delivery system for the administration of an antioxidant drug to a patient in need of such drug, wherein said delivery system comprises said drug in combination with a polymeric matrix, said matrix comprising a polymer which does not interact with said drug or a mixture of such polymers.

The invention further relates to methods of treating a patient suffering from increased formation of active oxygen species comprising administering to the patient a therapeutically effective amount of the pharmaceutical delivery system according to the invention.

DETAILED DESCRIPTION OF THE INVENTION

As described in the Background of the Invention, numerous problems are involved in preparing dosage forms of antioxidant drugs such as, for example vitamin E (α-tocopherol), which at present reduce their effectivity if and when used in the treatment of diseases.

The present inventors succeeded to incorporate such therapeutically active antioxidant drugs in a polymeric matrix and thus obtained a pharmaceutical delivery system which enables the administration of these drugs and their release at their biological targets in a sustained-release manner over prolonged periods of time.

The invention relates to a sustained-release pharmaceutical delivery system for the administration of an antioxidant drug to a patient in need of such drug, wherein said delivery system comprises said drug in combination with a polymeric matrix, said matrix comprising a polymer which does not interact with said drug, or a mixture of such polymers.

A great variety of polymers may comprise the polymeric matrix of the delivery system of the invention. These may be natural, modified natural or synthetic hydrophilic or hydrophobic polymers.

For example, the polymer may be a hydrophilic polymer such as, for example gelatin, ovalbumin, soybean proteins, gum Arabic, modified starch, methylcellulose, hydroxypropyl cellulose, hydroxypropylmethyl cellulose and like polymers and mixtures thereof, or a hydrophobic polymer such as a polyamide, polyacrylate, polyurethane, waxes, polypropylene, ethyl cellulose and like polymers and mixtures thereof, or mixtures of such hydrophilic and hydrophobic polymers.

The antioxidant drug may be any suitable drug which chemically neutralizes reactive oxygen species, thus reducing oxidative stress. Examples of such drugs are various forms of vitamin E, such as α-d-tocopherol, α-dl-tocopherol, α-d-tocopherol acetate, α-dl-tocopherol acetate or α-d-tocopherol acid succinate, ascorbic acid, β-caroten and selenium. In a preferred embodiment the active drug is any of said forms of vitamin E or combinations thereof.

The above mentioned polymers do not interact with the active antioxidant drug and therefore release of the active drug from a matrix consisting of said polymers would not be dependent upon the rate of decomposition of a chemical bond between the polymeric matrix, and the drug, which may be influenced by changing conditions of the environment. For example, in orally administerable forms, the conditions in the gastrointenstinal tract, e.g., pH, concentration of salts, etc., may substantially influence any chemical reaction.

Moreover, both the chemical and physical properties of matrices comprised of the said polymers, such as permeability and solubility, are not influenced by pH and other changes. This resistance of the matrices of the invention to environmental conditions renders them particularly suitable for the desired purpose.

In addition, the chemical properties of the polymeric matrices according to the invention enable the incorporation thereinto of active agents in liquid phase (for example vitamin E). This is particularly advantageous in preparing the delivery systems in accordance with the invention.

The pharmaceutical delivery system according to the invention may be formulated in various formulations, including dosage unit forms, which may be suitable for oral, local or transdermal administration as well as implants.

The various formulations may be prepared by mixing the polymer or mixture of polymers with the active antioxidant drug, by methods as described in the following examples as well as by other methods known to the man versed in the art.

Specific embodiments of orally administerable formulations of the delivery system according to the invention include, for example, matrix-drug tablets, matrix-drug pellets and matrix-drug nanoparticles, either free or packed in gelatin capsules or other means enabling oral administration, and multi-layered coated tablets. All of the said embodiments may be coated with biodegradable coating polymers. The said coating polymers may be, for example, the polymers comprising the said matrix, polymers affording protection against gastric pH and enzymes, transition metals and the like. The coating layer may be applied to the dosage form, for example, by spray-coating, molding or double pressing techniques, all of which techniques are known in the art.

In addition to oral dosage forms, the delivery system of the present invention may be adapted to dosage forms for local, for example opthalmic, and transdermal administration, as well as implants which will release the active antioxidant drug in a controlled manner. Particular forms suitable for such administration include, for example, films. The preparation of films in accordance with the invention is described in the following examples. As may be seen from Table 4, which details the results of release of vitamin E from films according to the invention, preparation of the films from ethanolic solutions of the polymers and the drug gives films from which vitamin E is released faster than from films prepared from chloroformic solutions. The drug is also released faster from films comprising polyethylene glycol.

The amount of active antioxidant drug can vary as desired for a therapeutically effective amount and may depend on the patient's age, sex, weight, physical condition, disease or condition to be treated, and other medical criteria as well as on the relative efficacy of the drug. This effective amount may be determined by techniques known in the art. For example, in case the antioxidant drug is vitamin E, the amount of the drug is a dosage unit form may be from about 10 IU to about 1000 IU.

The rate of release of the active antioxidant drug from the delivery system of the invention can be adjusted by varying the relative concentrations of its constituents. This is a major advantage of the present delivery system. For example, release from existent tablet-form preparations is fast, and about 86% of the active agent are released within about 30 minutes. Using the polymeric matrix of the invention with, for example, Methocel® and egg albumin, enables the preparation of tablets with sustained-release of the active agent. The inventors have found out that increase of the concentration of the active agent or addition of polyethylene glycol (PEG) increase the rate of release. In particular embodiments, the polymeric matrix constitutes from about 20% to about 80% (w/w) of the pharmaceutical delivery system of the invention.

The various dosage forms according to the invention may be prepared and tested by techniques will known in the art. In any case, in all embodiments it is possible, if desired, to include more than a single drug to be administered to the patient within the same matrix.

The delivery system of the invention may be used for treating various pathological conditions. For example, delivery systems comprising vitamin E as the drug, may be used for the treatment of, for example, various cancers (stomach, lung, colon), esophagal dysphasia, stroke, cataract, gastric mucosal injury, oral leukoplakia, Parkinson's disease and related neurological disorders, cardiac disorders and tardive dyskinesia. Administration of antioxidant drugs, enabled by the delivery system of the invention, is also expected to increase the life span of the treated patient.

The invention further relates to methods of treating a patient suffering oxidative stress by administering to the patient a therapeutically effective amount of the pharmaceutical delivery system of the invention. By the term administration is meant administration via oral, local and transdermal routes, in a controlled manner.

The delivery system and method of the invention are not limited to humans and may be especially useful for veterinary administration of vitamins and other antioxidants to animals, particularly domestic animals and pets.

The following Examples describe the materials and methods used in carrying out the invention. The examples are illustrative only and do not in any sense limit the invention which is only defined by the appended claims.

EXAMPLES

Example 1

Preparation of films containing Vitamin E

Ethyl cellulose and polyethylene glycol, and/or acrylic and methacrylic esters (Eudragit®) polymers were dissolved by slowly adding dry powders to vigorously stirred ethanol or chloroform. After complete dissolution of the polymers α-tocopherol (vitamin E) was added. The total vitamin E and polymers concentration was 6% (w/v).

Films were cast by pouring the ethanolic solution onto glass plates and allowing the solvent to evaporate at room temperature. The resulting films were then removed from the glass plates. The different film formulations are summarized in Table 1.

TABLE 1

Vitamin E Sustained-Release Film Formulations

| | % (w/w) in dry film | | | | | Thickness |
|---|---|---|---|---|---|---|
| Formulation | Vit. E | EC* | Eudragit RL | PEG 400 | Chloroform | EtOH | (μ) |
| 1 | 30 | 70 | — | — | + | — | 30 |
| 2 | 30 | 70 | — | — | + | — | 50 |
| 3 | 30 | 70 | — | — | + | — | 120 |
| 4 | 30 | 70 | — | — | + | — | 200 |
| 5 | 20 | 80 | — | — | + | — | 120 |
| 6 | 10 | 90 | — | — | + | — | 120 |
| 7 | 30 | 65 | — | 5 | + | — | 120 |
| 8 | 30 | 70 | — | — | — | + | 120 |
| 9 | 30 | 70 | — | — | — | + | 200 |
| 10 | 30 | 65 | — | 5 | — | + | 120 |
| 11 | 30 | — | 70 | — | — | + | 50 |
| 12 | 30 | — | 70 | — | — | + | 120 |
| 13 | 20 | — | 80 | — | — | + | 120 |
| 14 | 30 | — | 65 | 5 | — | + | 120 |
| 15 | 30 | — | 60 | 10 | — | + | 120 |
| 16 | 30 | — | 50 | 20 | — | + | 120 |
| 17 | 30 | — | 70 | — | + | — | 120 |
| 18 | 30 | 20 | 50 | — | — | + | 120 |
| 19 | 30 | 35 | 35 | — | — | + | 120 |
| 20 | 30 | 40 | 30 | — | — | + | 120 |
| 21 | 30 | 50 | 20 | — | — | + | 120 |

*EC-Ethyl cellulose

Preparation of tablets containing vitamin E

The vitamin E formulations were prepared in matrix tablet form with hydroxypropylmethyl cellulose or egg albumin carriers. The tablets were prepared by mixing the ingredients in desired proportions until a homogenous mixture was obtained. The mixture was compressed by a manual hydraulic press under 8,000 kg and tablets obtained by using a 12 mm punch and die. The total weight each tablet exemplified herein was 600 mg. The various sustained-release tablets which were prepared are summarized in Table 2.

TABLE 2

Composition of Vitamin E Tablets

| Formulation | Vit E (IU)-% w/w | Methocel$^{R*}$ % w/w | Egg Albumin % w/w | PEG 4000 % w/w |
|---|---|---|---|---|
| 22 | 360 60 | 40 | — | — |
| 23 | 360 60 | 20 | — | 20 |
| 24 | 180 30 | 70 | — | — |
| 25 | 120 20 | 40 | — | 40 |
| 26 | 60 10 | 45 | — | 45 |
| 27 | 360 60 | — | 40 | — |
| 28 | 360 60 | — | 20 | 20 |
| 29 | 180 30 | — | 70 | — |
| 30 | 180 30 | — | 35 | 35 |
| 31 | 120 20 | — | 40 | 40 |

*Hydroxypropylmethyl cellulose

Dissolution rate studies

1. Rates of release of vitamin E from tablets

Dissolution tests were carried out using the rotating basket method [USP XX]. 900 ml of phosphate buffer pH 7.2 containing 20% (v/v) of ethanol, contained in a 1000 ml flask, rotated at constant velocity of 100 rpm, at 37° C., served as the dissolution medium (USP XX, Apparatus I).

At suitable intervals 5 ml samples were removed, diluted as required, and the concentration of vitamin E was determined spectrophotometrically (UV spectophotometer) at 284 nm. Results are summarized in Table 3.

TABLE 3

Release Rates of Vitamin E from Sustained-Release Tablets (% released)

| | Time (h) | | | | | | | | | |
|---|---|---|---|---|---|---|---|---|---|---|
| | 0.5 | 1 | 2 | 3 | 4 | 5 | 6 | 7 | 8 | 12 | 24 |
| Stn.* | 85.6 | 98.3 | | | | | | | | | |
| 22 | 13.2 | 18.3 | 28.1 | 38.4 | 49.3 | 56.7 | 60.9 | 63.4 | 75.1 | 92.7 | |
| 23 | 24.6 | 52.7 | 68.3 | 92.1 | 98.8 | | | | | | |
| 24 | 10.8 | 13.4 | 25.0 | 31.7 | 36.1 | 38.0 | 48.1 | | | | |
| 25 | 6.3 | 9.1 | 13.2 | 18.9 | 25.3 | 27.4 | 32.5 | 32.6 | 41.3 | 68.7 | 98.9 |
| 26 | 3.7 | 5.2 | 9.4 | 12.1 | 19.4 | 23.7 | 26.9 | 31.9 | 36.8 | 62.3 | 86.1 |
| 27 | 6.2 | 10.7 | 18.4 | 27.1 | 39.1 | 48.3 | 54.8 | 59.2 | 63.5 | 80.4 | 99.5 |
| 28 | 7.9 | 12.0 | 23.4 | 37.1 | 48.7 | 61.4 | 74.1 | 86.9 | 95.7 | | |
| 29 | 3.3 | 6.9 | 13.1 | 18.5 | 26.1 | 33.9 | 37.5 | 43.2 | 50.6 | 76.1 | 86.9 |
| 30 | 2.5 | 5.9 | 11.1 | 14.4 | 16.3 | 18.1 | 19.2 | 21.4 | 22.8 | 35.6 | 59.3 |
| 31 | 1.8 | 2.5 | 5.7 | 9.8 | 12.1 | 15.6 | 17.7 | 19.7 | 21.1 | 30.9 | 48.9 |

Stn* = Standard: Tega E Capsules (Ortega)-400 IU Vitamin E

2. Rates of release of vitamin E from films

Films containing vitamin E were cut to 1 cm² rectangles, and their thickness and weight were measured. Rates of release of vitamin E from the films were measured in glass vials containing 2.5 ml of phosphate buffer pH 7.2 containing 20% (v/v) ethanol in an orbital shaker at 37° C. and rotating velocity of 100 rpm.

5 ml samples were removed at various time intervals and replaced by equal volumes of same buffer, in order to maintain a constant volume. The concentration of vitamin E was determined by spectrophotometrically (UV spectophotometer) at 284 nm. Results are summarized in Table 4.

consisting of α-d-tocopherol, α-dl-tocopherol, α-d-tocopherol acetate, α-dl-tocopherol acetate, α-d-tocopherol acid succinate, ascorbic acid, β-caroten and selenium or mixtures thereof.

7. A pharmaceutical delivery system according to claim 6 wherein said antioxidant drug is α-tocopherol, α-dl-tocopherol, α-d-tocopherol acetate, α-dl-tocopherol acetate or α-d-tocopherol acid succinate or any mixture thereof.

8. The pharmaceutical delivery system according to claim 1 further comprising a pharmaceutically acceptable carriers or additives.

TABLE 4

Release Rates of Vitamin E from Sustained-Release Films (% released)

| | Time (h) | | | | | | | | | | | |
|---|---|---|---|---|---|---|---|---|---|---|---|---|
| | 0.5 | 1 | 2 | 3 | 4 | 5 | 6 | 7 | 8 | 24 | 48 | 72 |
| 1 | 25.4 | 68.7 | 98.9 | | | | | | | | | |
| 2 | 15.9 | 34.8 | 63.1 | 72.1 | 79.3 | 85.0 | 86.7 | 90.1 | 92.1 | 99.2 | | |
| 3 | 11.2 | 17.3 | 25.0 | 32.1 | 37.1 | 44.0 | 47.1 | 52.3 | 56.1 | 85.1 | 97.9 | |
| 4 | 2.4 | 4.9 | 8.1 | 11.2 | 14.7 | 18.1 | 21.0 | 23.1 | 27.2 | 55.3 | 77.2 | 83.6 |
| 5 | 9.7 | 14.8 | 20.2 | 28.7 | 31.0 | 37.1 | 39.8 | 44.0 | 46.3 | 73.4 | 86.4 | 92.1 |
| 6 | 7.2 | 12.0 | 16.6 | 22.1 | 25.4 | 29.0 | 32.4 | 35.1 | 37.0 | 59.2 | 68.7 | 79.2 |
| 7 | 12.9 | 20.4 | 28.6 | 36.1 | 42.2 | 48.6 | 53.1 | 57.4 | 61.0 | 92.1 | | |
| 8 | 36.1 | 40.6 | 57.2 | 68.1 | 76.2 | 81.2 | 85.0 | 89.6 | 99.7 | | | |
| 9 | 6.8 | 12.3 | 16.1 | 20.9 | 25.4 | 30.0 | 34.1 | 37.0 | 40.0 | 68.1 | 97.1 | |
| 10 | 19.1 | 39.7 | 44.2 | 62.9 | 74.7 | 84.0 | 89.2 | 92.1 | 99.6 | | | |
| 11 | 15.2 | 25.4 | 34.6 | 42.1 | 49.2 | 56.0 | 60.7 | 71.0 | 75.1 | 88.4 | 97.9 | |
| 12 | 10.8 | 17.6 | 24.2 | 32.7 | 42.1 | 48.2 | 54.6 | 58.1 | 63.6 | 70.9 | 84.2 | 91.3 |
| 13 | 9.2 | 15.2 | 21.8 | 28.1 | 43.9 | 39.1 | 43.6 | 47.1 | 50.6 | 60.2 | 71.6 | 79.0 |
| 14 | 11.9 | 19.7 | 33.5 | 45.9 | 55.4 | 65.8 | 70.6 | 75.0 | 83.0 | 90.1 | 98.9 | |
| 15 | 13.1 | 21.8 | 36.8 | 50.4 | 60.9 | 62.8 | 77.1 | 82.1 | 92.0 | 96.4 | | |
| 16 | 15.7 | 26.4 | 44.2 | 60.1 | 70.2 | 76.1 | 92.0 | 96.8 | | | | |
| 17 | 5.4 | 8.1 | 12.0 | 17.1 | 21.2 | 24.0 | 27.1 | 29.0 | 31.8 | 35.0 | 42.6 | 50.3 |
| 18 | 12.3 | 21.1 | 27.9 | 37.3 | 48.8 | 55.4 | 62.8 | 66.8 | 72.4 | 81.4 | 96.9 | |
| 19 | 14.1 | 24.2 | 32.1 | 42.8 | 51.4 | 63.7 | 72.1 | 76.1 | 83.4 | 95.8 | | |
| 20 | 15.2 | 26.3 | 35.4 | 46.3 | 56.7 | 79.0 | 79.2 | 83.7 | 91.6 | | | |
| 21 | 16.9 | 28.4 | 39.7 | 50.9 | 62.1 | 77.4 | 88.1 | 91.9 | | | | |

We claim:

1. A sustained release pharmaceutical delivery system for the administration of an antioxidant drug to a patient in need of such drug, wherein said delivery system comprises said drug in combination with a matrix, said matrix comprising a polymer selected from the group consisting of a polymer which does not interact with said rug and a mixture of such polymers, and said polymeric matrix is present in amounts from about 20% (w/w) to about 80% (w/w).

2. A pharmaceutical delivery system according to claim 1 wherein said polymer is a hydrophilic polymer selected from the group consisting of gelatin, ovalbumin, soybean proteins, gum Arabic, modified starch, methylcellulose, hydroxypropyl cellulose and hyroxypropylmethyl cellulose or a hydrophobic polymer selected from the group consisting of polyamides, polyacrylates, polyurethan, waxes, polypropylene and ethyl cellulose or any mixture thereof.

3. A pharmaceutical delivery system according to claim 1 in dosage unit form.

4. A pharmaceutical delivery system according to claim 3 in the form of a tablet, which tablet may be optionally coated with a suitable protective coating.

5. A pharmaceutical delivery system according to claim 3 in film form.

6. A pharmaceutical delivery system according to claim 1 wherein said antioxidant drug is selected from the group 9. The pharmaceutical delivery system according to claim 1 for the treatment of pathological conditions involving pathologically increased formation of active oxygen species.

10. A method of treating pathological conditions involving pathologically increased formation of active oxygen species comprising administering to a patient in need of such treatment a therapeutically effective amount of the pharmaceutical delivery system according to claim 1.

11. A sustained release pharmaceutical delivery system for the administration of an antioxidant drug to a patient in need of such drug, wherein said delivery system comprises said drug in combination with a matrix, said matrix comprising a polymer selected from the group consisting of a polymer which does not interact with said drug and a mixture of such polymers, and said antioxidant drug is present in amounts of from about 100 IU to about 1000 IU.

12. The pharmaceutical delivery system according to claim 11 for the treatment of pathological conditions involving pathologically increased formation of active species.

13. The pharmaceutical delivery system according to claim 1 wherein the antioxidant drug is present in amounts of from about 100 IU to about 1000 IU.

* * * * *